United States Patent [19]

Reynolds

[11] Patent Number: 4,959,013

[45] Date of Patent: Sep. 25, 1990

[54] RECYCLING, LIQUID MEDIUM TEMPERATURE ALTERING APPARATUS

[75] Inventor: Fred W. Reynolds, San Pedro, Calif.

[73] Assignee: Sol Gingi-Pak, A Division of Belport Co., Inc., Camarillo, Calif.

[21] Appl. No.: 237,373

[22] Filed: Aug. 29, 1988

[51] Int. Cl.⁵ ............................................... A61C 9/00
[52] U.S. Cl. ........................................ 433/35; 62/299; 62/435; 164/126; 128/400
[58] Field of Search ............... 433/35; 128/66, 400; 164/126, 128, 348, 443; 62/299, 435

[56] References Cited

U.S. PATENT DOCUMENTS

| 39,673 | 8/1963 | Oudry | 433/35 |
| 2,863,215 | 12/1958 | Lane | 433/35 |
| 3,762,411 | 10/1973 | Lloyd et al. | 128/66 |
| 3,783,937 | 1/1974 | Maurer | 164/128 |
| 4,109,650 | 8/1978 | Peclard | 128/66 |

FOREIGN PATENT DOCUMENTS 18607   4/1900   United Kingdom .................. 433/35

Primary Examiner—John J. Wilson
Attorney, Agent, or Firm—Jack C. Munro

[57] ABSTRACT

A self-contained apparatus which includes a liquid reservoir and a liquid supply conduit and a liquid return conduit to the reservoir. The liquid is to be supplied to an exterior structure for changing the temperature of the exterior structure. The reservoir is to be removable from the apparatus to facilitate filling of the reservoir.

5 Claims, 1 Drawing Sheet

U.S. Patent  Sep. 25, 1990  4,959,013
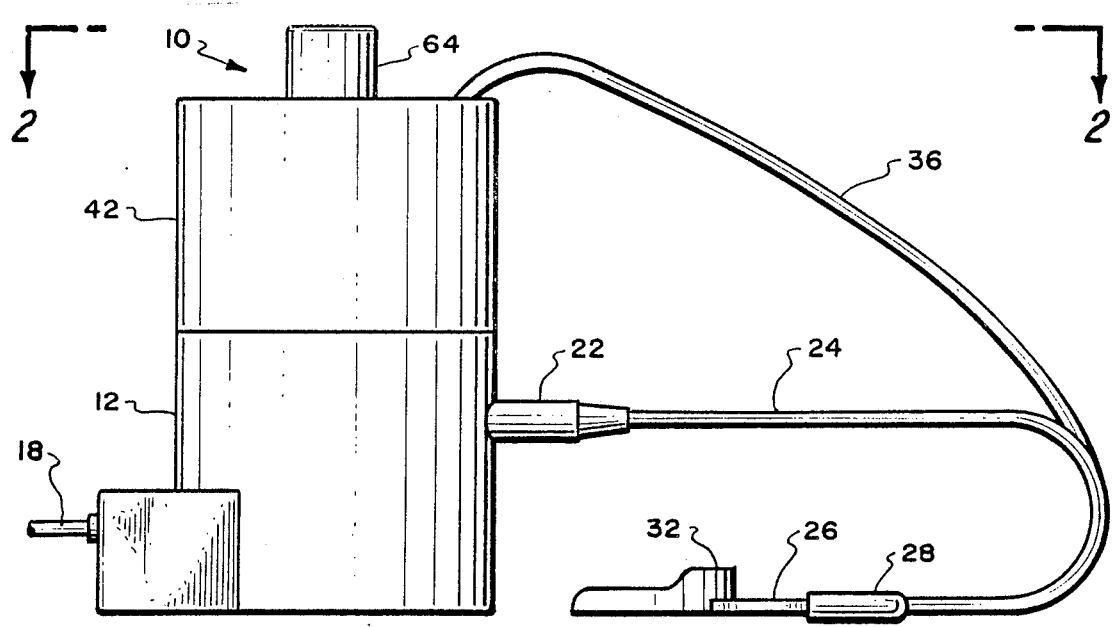
Fig. 1
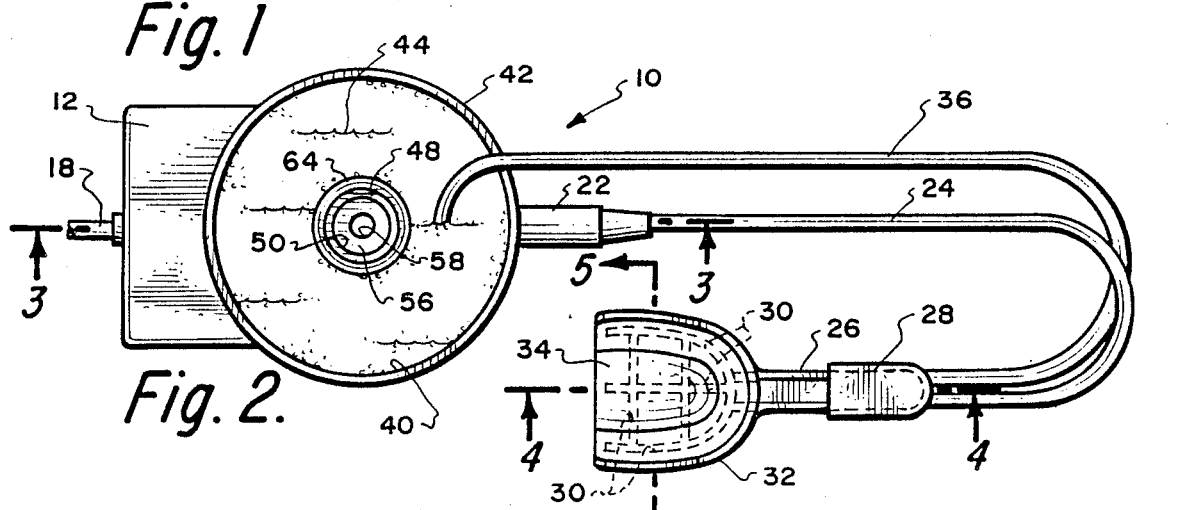
Fig. 2
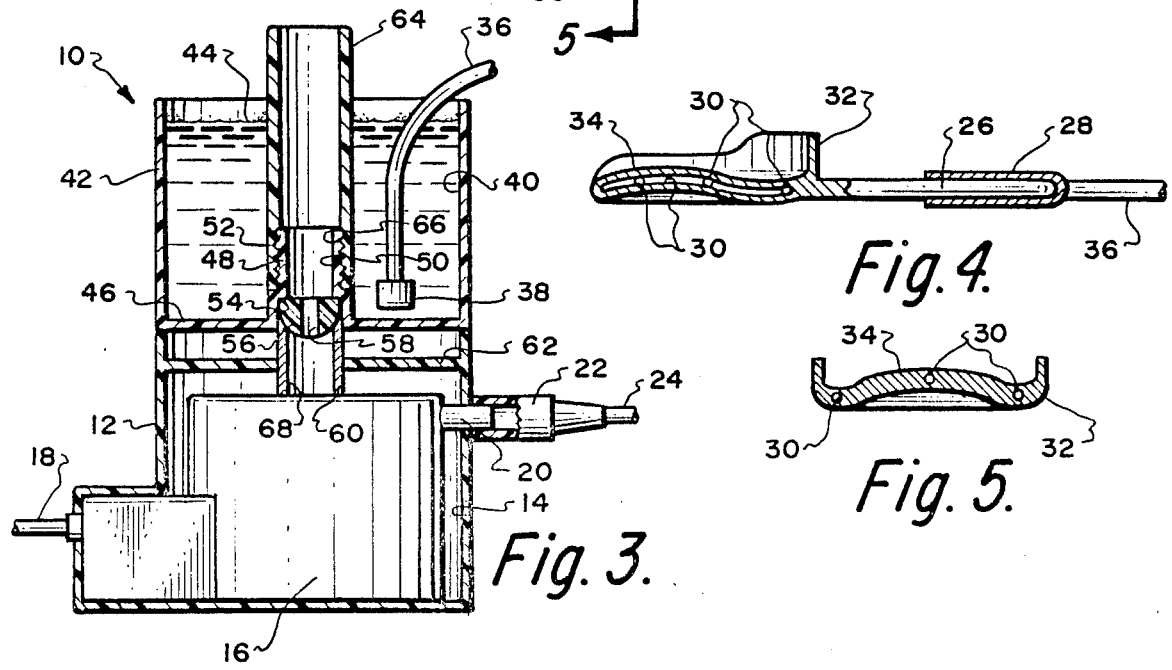
Fig. 3
Fig. 4
Fig. 5

RECYCLING, LIQUID MEDIUM TEMPERATURE ALTERING APPARATUS

BACKGROUND OF THE INVENTION

The field of this invention relates to an apparatus for altering of the temperature of an exterior structure and more particularly to an apparatus for the cooling of a dental tray which is used in making dental impressions.

The subject matter of this invention will be discussed primarily in conjunction with the dental field. However, it is to be understood that the subject matter could be utilized in other fields and Applicant does not intend to solely restrict the subject matter of this invention to the dental field.

In the field of dentistry, it is exceedingly common to make impressions of portions of the mouth of a human being. These impressions are then utilized to make dental appliances such as bridges, crowns, caps, etc. In the making of these dental impressions, it is common to use a hydrocolloid. Hydrocolloid is composed of natural ingredients and in essence is a water base gelatin. The impression by the hydrocolloid is quite accurate.

The procedure in using the hydrocolloid is to take the hydrocolloid at room temperature and raise its temperature to where it assumes a liquefied state. This now liquefied hydrocolloid is then placed within a dental tray which is in a particular configuration such as the shape of a portion of the mouth of a human being. Once this hydrocolloid has assumed the temperature of about one hundred thirty degrees Fahrenheit, it is capable of being inserted within the mouth of the patient. The area of the mouth of which an impression is desired is pressed into the hydrocolloid with the result that the hydrocolloid will flow completely around this area of the mouth making a very accurate impression.

The tray and the hydrocolloid is now permitted to cool. It is common that such trays include a water passage arrangement and water is to be supplied to the tray from a dedicated source, such as a normal water supply conduit, with the water being then discharged into a sewer line. Generally, this cooling takes a period of a few minutes, such as three to four minutes. During this period of time a substantial amount of water will be conducted through the dental tray and disposed into the sewer line. This is wasteful because no use is made of the water with the exception of the function as a cooling medium.

Also, in order to use the dental tray there had to be a source of water nearby. This meant that unless plumbing was in close proximity of the patient, that cooling of the dental tray could not be accomplished in a matter of a few minutes but would require a substantially longer length of time since water could not be passed through the dental tray.

SUMMARY OF THE INVENTION

One of the primary objectives of the present invention is to construct a portable dental tray cooling apparatus which would permit the dental tray to be quickly and easily cooled in areas in which plumbing within the dentist's office was not readily available.

Another objective of the present invention is to construct a dental tray cooling device which recycles the cooling water and thereby eliminates the waste of water in conjunction with the prior art cooling technique.

The apparatus of this invention relates to a housing within which is mounted a pump. A water supply inlet passage and an outlet passage is mounted within the housing and connected to the pump. A reservoir is removably mounted in conjunction with the housing. The reservoir is to be filled or cleaned at a separate location and then is to be installed in conjunction with the housing. The water is supplied to the pump which is then conducted through the outlet into a conduit to a water cooling passage arrangement within a dental impression tray and then back through a conduit into the reservoir.

BRIEF DESCRIPTION OF THE DRAWING

FIG. 1 is a side elevational view of the apparatus of the present invention showing such connected in conjunction with a dental tray;

FIG. 2 is a top plan view of the apparatus of the present invention taken along line 2—2 of FIG. 1;

FIG. 3 is a cross-sectional view through the reservoir and housing of the apparatus of the present invention taken along line 3—3 of FIG. 2;

FIG. 4 is a longitudinal cross-sectional view through the dental tray utilized in conjunction with the apparatus of the present invention taken along line 4—4 of FIG. 2; and FIG. 5 is a transverse cross-sectional view through the dental tray utilized in conjunction with the apparatus of the present invention taken along line 5—5 of FIG. 2.

DETAILED DESCRIPTION OF THE SHOWN EMBODIMENT

Referring particularly to the drawing there is shown the apparatus 10 of this invention which includes a thin walled plastic housing 12. Housing 12 includes an internal chamber 14. Within the internal chamber 14 is located a pump 16. Pump 16 is driven electrically through conductor 18 which is connected an external source of electrical energy (not shown).

Connected to the pump 16 is an outlet 20. This outlet 20 extends through the wall of the housing 12 and connects with a connector 22. Connector 22 connects with a conduit 24 the outer end of which is attached to tray extension 26. Tray extension 26 will normally be constructed of metal. A cover strip 28 secures conduit 24 onto the tray extension 26. Through the tray extension 26 is a liquid conducting passage which connects with the liquid passage arrangement 30 of the dental tray 32. The dental tray 32 is also formed of metal and is integral with the tray extension 26. The dental tray includes a mold cavity 34.

The liquid passage arrangement 30 connects to an outlet passage which passes through the tray extension 26 and connects with return conduit 36. Return conduit 36 terminates at a diffuser 38. This diffuser 38 rests within internal chamber 40 of a liquid reservoir 42. Internal chamber 40 is to contain a liquid, such as water 44.

Centrally mounted within the bottom wall 46 of the reservoir 42 is an outlet tube 48. This tube 48 includes an internal opening 50 and a series of external threads 52. Formed within the bottom wall 46, directly adjacent the opening 50, is a recess 54. Within this recess 54 is located a rubber or plastic sealing member 56. The sealing member 56 has an exterior rounded configuration and has an internal hole 58. The external surface of the sealing member 56 is to tightly abut against and form a liquid-tight seal with tube 60. Tube 60 is to constitute the inlet conduit for the pump 16. The tube 60 is fixedly mounted within upper wall 62 of the housing 12. With the seal 56 in tight engagement with the tube 60, the reservoir 42 will merely rest on the upper portion of the housing 12.

The diffuser 38 can be removed from the internal chamber 50. A tubular handle member 64 includes a series of internal threads 66. These threads 66 are to threadably connect with the threads 52. With the handle member 64 threadably connecting with tube 48, an individual can grasp the handle 64 and disengage the seal 56 from the tube 60 and move the reservoir 42 to a location spaced from the housing 12. At this time, the internal chamber 40 can be either refilled with water 44 and/or can be cleaned.

Upon the internal chamber 40 being refilled with water 44, the user, by grasping of handle member 64, can replace the seal 56 in connection with the tube 60. At this time the user then unscrews the handle member 64 from the tube 48 which will permit the water 44 to flow through openings 50, 58, into passage 68 of tube 60 and into the pump 16. Therefore, by activating of the pump 16, water is then permitted to flow into conduit 24 into the liquid passage arrangement 30 of the dental tray 32 and then back through the return conduit 36 into the internal chamber 40. It can thus be seen that there is a recycling closed system for the water 44.

This water 44 can quickly and easily affect cooling of the dental tray 32. It is to be understood that within the mold cavity 34 of the dental tray 32 there will be located a quantity of a substance to be cooled such as hydrocolloid (not shown).

What is claimed is:

1. An apparatus for subjecting an exterior structure to a change in temperature comprising:
    an exterior structure to be changed in temperature, said exterior structure having a liquid passage arrangement;
    a housing, a pump connected to said housing, a conduit assembly connecting said pump and said liquid passage arrangement;
    a liquid, said pump for moving said liquid through said conduit assembly and said passage arrangement;
    a reservoir, said liquid to be contained within said reservoir, said reservoir being connected by connecting means to said housing, said conduit assembly connecting with said reservoir, said conduit assembly and said pump and said reservoir and said liquid passage arrangement forming a closed liquid conducting system; and
    said reservoir being removably mounted directly on said housing.

2. An apparatus for subjecting an exterior structure to a change in temperature comprising:
    an exterior structure to be changed in temperature, said exterior structure having a liquid passage arrangement;
    a housing, a pump connected to said housing, a conduit assembly connecting said pump and said liquid passage arrangement;
    a liquid, said pump for moving said liquid through said conduit assembly and said liquid passage arrangement;
    a reservoir, said liquid to be contained within said reservoir, said reservoir being connected by connecting means to said housing, said conduit assembly connecting with said reservoir, said conduit assembly and said pump and said reservoir and said liquid passage arrangement forming a closed liquid conducting system;
    said reservoir being removably mounted on said housing; and
    a sealing means mounted on said reservoir, a pump inlet passage mounted within said housing, said pump inlet passage to connect with said pump, said sealing means to form a liquid-tight connection between said reservoir and said housing with said reservoir being mounted on said housing.

3. An apparatus for subjecting an exterior structure to a change in temperature comprising:
    an exterior structure to be changed in temperature, said exterior structure having a liquid passage arrangement;
    a housing, a pump connected to said housing, a conduit assembly connecting said pump and said liquid passage arrangement;
    a liquid, said pump for moving said liquid through said conduit assembly and said liquid passage arrangement;
    a reservoir, said liquid to be contained within said reservoir, said reservoir being connected by connecting means to said housing, said conduit assembly connecting with said reservoir, said conduit assembly and said pump and said reservoir and said liquid passage arrangement forming a closed liquid conducting system;
    a reservoir being removably mounted on said housing; and
    said reservoir including a handle, said handle being removably disconnected from said reservoir, said housing including a pump inlet passage, said pump inlet passage to supply liquid to said pump, with said handle being connected to said reservoir and said reservoir being mounted on said housing said liquid not being permitted to flow into said pump inlet passage, with said handle being disconnected from said reservoir said liquid being flowable from said reservoir into said pump inlet passage.

4. The apparatus as defined in claim 3 wherein: said exterior structure comprising a dental tray.

5. The apparatus as defined in claim 4 wherein: said liquid comprising water.

* * * * *